United States Patent
Da

(10) Patent No.: US 12,292,442 B2
(45) Date of Patent: May 6, 2025

(54) MONOCLONAL ANTIBODY AGAINST CD19 ANTIBODY AND APPLICATION THEREOF

(71) Applicant: BIOSWAN LABORATORIES, INC., Shanghai (CN)

(72) Inventor: Liang Da, Shanghai (CN)

(73) Assignee: BIOSWAN LABORATORIES, INC., Shanghai (CN)

( * ) Notice: Subject to any disclaimer, the term of this patent is extended or adjusted under 35 U.S.C. 154(b) by 822 days.

(21) Appl. No.: 17/416,974

(22) PCT Filed: Dec. 17, 2019

(86) PCT No.: PCT/CN2019/126087
§ 371 (c)(1),
(2) Date: Jun. 21, 2021

(87) PCT Pub. No.: WO2020/125653
PCT Pub. Date: Jun. 25, 2020

(65) Prior Publication Data
US 2022/0074937 A1    Mar. 10, 2022

(30) Foreign Application Priority Data

Dec. 20, 2018  (CN) .......................... 201811565418.1

(51) Int. Cl.
| | | |
|---|---|---|
| G01N 33/569 | (2006.01) | |
| C07K 16/28 | (2006.01) | |
| C07K 16/42 | (2006.01) | |

(52) U.S. Cl.
CPC ... *G01N 33/56972* (2013.01); *C07K 16/2803* (2013.01); *C07K 16/4258* (2013.01); *C07K 2317/565* (2013.01); *C07K 2317/92* (2013.01)

(58) Field of Classification Search
CPC ........ G01N 33/56972; C07K 2317/565; C07K 16/4241
See application file for complete search history.

(56) References Cited

FOREIGN PATENT DOCUMENTS

| | | | | |
|---|---|---|---|---|
| CN | 108490174 A | | 9/2018 | |
| CN | 108508200 A | * | 9/2018 | ......... C07K 16/2803 |
| WO | WO-2014190273 A1 | * | 11/2014 | ....... C07K 14/70503 |
| WO | WO-2018073267 A1 | * | 4/2018 | ............... G01N 1/28 |
| WO | 2020125653 A1 | | 6/2020 | |

OTHER PUBLICATIONS

Mariuzza (Annu. Rev. Biophys. Biophys. Chem., 16: 139-159, 1987) (Year: 1987).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Park et al (CD19-targeted CAR T-cell therapeutics for hematologic malignancies: interpreting clinical outcomes to date. Blood. Jun. 30, 2016;127(26):3312-20) (Year: 2016).*
FMC63, Acro Biosystems, obtained from: https://www.acrobiosystems.com/L-1046-FMC63.html?gad_source=1&gclid=EAlaIQobChMI2YWbherMiAMViaRaBR3vHSeUEAAYAyAAEgJWa_D_BwE (Year: 2024).*
International Search Report and Written Opinion; PCT Application No. PCT/CN2019/126087 mailed Mar. 18, 2020.
English translation of International Search Report; PCT Application No. PCT/CN2019/126087 mailed Mar. 18, 2020.
Sohma, Yoshiaki et al., "Accumulation of plasma cells in atherosclerotic lesions of Watanabe heritable hyperlipidemic rabbits", Proceedings of the National Academy of Sciences of USA; vol. 92; May 31, 1995; pp. 4937-4941.
Sohma, Yoshiaki et al., "Immunoglobulin kappa chain [Oryctolagus cuniculus], Accesion No. BAA07455.1", NCBI Genbank; Mar. 27, 2002.
Satiro N. De Oliveira, et al., "A CD19/Fc fusion protein for detection of anti-CD19 chimeric antigen receptors", Journal of Translational Medicine; vol. 11; Jan. 29, 2013.
English abstract of CN108508200; retrieved from www.espacenet.com on Jun. 21, 2021.
English abstract of CN108490174; retrieved from www.espacenet.com on Jun. 21, 2021.

* cited by examiner

*Primary Examiner* — Elizabeth C. Kemmerer
*Assistant Examiner* — Ashley H. Gao
(74) *Attorney, Agent, or Firm* — NKL Law; Allen Xue

(57) ABSTRACT

Provided are a monoclonal antibody against CD19 antibody and the application thereof. The monoclonal antibody which targets CD 19 antibody has high specificity and strong affinity. Also provided are a detection reagent with high sensitivity, good accuracy and good specificity for the detection of CAR-T cells and a detection method using the detection reagent, which may directly target an extracellular antigen-binding region on the CAR-T cell.

11 Claims, 7 Drawing Sheets

Specification includes a Sequence Listing.

| No. | Sensor | Loading sample | Conc. of R19mab (nM) | $K_d$ (M) |
|---|---|---|---|---|
| 0 | Ligand sensor |  | 15.6 |  |
| 1 | Ligand sensor | FMC63 scFv | 15.6 | 4.31E-11 |
| 2 | Ligand sensor | FMC63 scFv | 7.8 | 4.31E-11 |
| 3 | Ligand sensor | FMC63 scFv | 3.9 | 4.31E-11 |
| 4 | Ligand sensor | FMC63 scFv | 1.95 | 4.31E-11 |
| 5 | Ligand sensor | FMC63 scFv | 0.975 | 4.31E-11 |

MONOCLONAL ANTIBODY AGAINST CD19 ANTIBODY AND APPLICATION THEREOF

CROSS-REFERENCE TO RELATED APPLICATIONS

This application is a national stage entry of PCT/CN2019/126087 filed Dec. 17, 2019, which claims the benefit of Chinese Patent Application No. 201811565418.1, filed Dec. 20, 2018. The entire contents of each of the prior applications are herein incorporated by reference.

SEQUENCE LISTING

A Sequence Listing submitted herewith as an ASCII text file via EFS-Web is hereby incorporated by reference in accordance with 35 U.S.C. § 1.52 (e). The name of the ASCII text file for the Sequence Listing is "WO2020125653_Sequence listing. TXT", and the size of the ASCII text file is 7.8 KB.

TECHNICAL FIELD

The invention belongs to the field of biotechnology and medicine, in particular to a monoclonal antibody which anti-CD19 antibody and an application thereof.

BACKGROUND

With the development of tumor immunotherapy, chimeric antigen receptor (CAR)-T cell immunotherapy, which combines the advantages of antibodies and immune cells, has attracted great attention. CAR is mainly composed of extracellular antigen binding region and intracellular signal transduction region through hinge region and transmembrane region. The extracellular antigen binding region has the function of specifically recognizing and binding the target cell surface antigen. Its composition originates from the single chain variable domain (scFv) of the monoclonal antibody, and is composed of the heavy chain variable region ($V_H$) and light chain variable region ($V_L$). Intracellular signal transduction region is mainly composed of costimulatory signal and CD3zeta chain of T cell receptor (TCR). After CAR-expressing T (CAR-T) cells bind to target cell antigen through scFv, the intracellular signal transduction region transmits signals to T cells, thereby activating T cells, secreting perforins, granzymes and cytokines, etc., and exerting killing effects. At present, FDA has approved two CAR-T cell drugs, namely Kymriah of Novartis and Yescarta of Gilead. Both drugs target CD19-positive B-cell tumors and use the same antigen binding region, which is the scFv derived from the mouse monoclonal antibody FMC63.

The construction of CAR-T cells requires the transfection of CAR genes through viral or non-viral systems and integration into the T cell genome. When the gene is normally expressed and a transmembrane CAR structure is formed on the cell membrane, CAR-T cells have the activity of recognizing and killing target cells. Therefore, accurate detection of CAR-expressing positive T cells is a key step in CAR-T drug quality control, and is also an important link in clinical patient treatment dose control, process monitoring and auxiliary diagnosis. There are two common detection methods: detecting CAR gene positive T cells and detecting CAR protein positive T cells.

Detection of CAR gene positive T cells: Quantitative real time PCR (qPCR) is the main method to detect CAR gene positive T cells. The integrated CAR gene in cell genome and the copy number of CAR gene can be detected by qPCR. However, this method cannot accurately reflect the positive T cells expressing CAR, because some T cells integrated with CAR gene do not normally express CAR (Jennifer N. Brudno, et al., *Journal of Clinical Oncology*, 2016), false positives caused by these T cells reduce the accuracy of qPCR method application. More seriously, the qPCR method cannot distinguish CAR-positive T cells from CAR-positive B cells, which makes it difficult to find the risk of treatment and recurrence caused by CAR-positive B cells (Marco Ruella, et al., *Nature Medicine*, 2018). In addition, qPCR method cannot meet the demand of simultaneous detection of multiple surface markers (CD3, CD4, CD8, etc.) of T cells, which further limits the application of qPCR method.

Detection of CAR protein positive T cells: existing detection reagents include anti-mouse IgG (Fab')$_2$ (Jackson ImmunoResearch, Inc.), Protein L (Zhili Zheng, et al., *Journal of Translational Medicine*, 2012), CD19/Fc (Satiro N De Oliveira, et al., *Journal of Translational Medicine*, 2013), GFP-CD19 (patent application No. 201610354642.0), murine monoclonal antibody 136.20.1 (PCT/US2014/039365; Bipulendu Jena, et al., *PLoS One*, 2013). Among them, anti-mouse IgG (Fab')$_2$ and protein L was not sensitive to CD19 CAR, and could not distinguish different CAR (such as CD22 CAR, BCMA CAR, etc.) constructed by different mouse original scFv. Both CD19/Fc and GFP-CD19 depend on the binding of CD19 protein to FMC63 scFv on CD19 CAR, because the affinity of scFv to CD19 is significantly lower than that of intact antibody FMC63 to CD19 (IAN C. Nicholson, et al., *Molecular Immunology*, 1997), so the sensitivity of CD19/Fc and GFP-CD19 in detecting CD19 CAR is lower. The detection of mouse original CD19 CARmonoclonal antibody 136.20.1 depends on the binding of the antibody to FMC63 scFv on CD19 CAR, and the detection sensitivity is close to 1:1000, that is, one positive cell can be detected in 1000 cells. Its application in the detection of CD19 CAR positive cell in vivo still has the defect of low sensitivity. All of the above reagents have a small range of applications due to their own insurmountable reasons.

Therefore, it is urgent to develop CAR positive cell detection reagents and detection methods with high detection sensitivity and accuracy in this field to meet the requirements of CAR-T drug quality control, clinical treatment and auxiliary diagnosis.

SUMMARY OF THE INVENTION

The purpose of the present invention is to provide a CAR positive cell detection reagent with high detection sensitivity and high accuracy and application thereof.

In the first aspect of the present invention, there is provided a heavy chain variable region of an antibody comprising the following three complementarity determining regions or CDRs:

CDR1 as shown in

SEQ ID NO: 3:
                                 (SEQ ID NO: 3)
GIDFRNYG;

CDR2 as shown in

SEQ ID NO: 4:
                                 (SEQ ID NO: 4)
FSSSGST;

and
CDR3 as shown in

SEQ ID NO: 5:

```
                                            (SEQ ID NO: 5)
ARHPGPTNGWKL.
```

In another preferred embodiment, the heavy chain variable region has the amino acid sequence as shown in SEQ ID NO: 9.

```
                                            (SEQ ID NO: 9)
QSLEESGGRLVTPGTPLTLTCTVSGIDFRNYGVSWVRQAPGKGLEWIGI

FSSSGSTYYATWAKGRFTISKASSTTVDLKMTSLTTEDTATYFCARHPG

PTNGWKLWGPGTLVTVSS
```

In the second aspect of the present invention, there is provided a heavy chain of an antibody having the heavy chain variable region according to the first aspect of the present invention and a heavy chain constant region.

In another preferred embodiment, the heavy chain constant region is of rabbit origin, mouse origin or human origin.

In the third aspect of the present invention, there is provided a light chain variable region of an antibody having a complementarity determining regions or CDRs selected from the group consisting of:
CDR1' as shown in

SEQ ID NO: 6:

```
                                            (SEQ ID NO: 6)
QSVSGY;
```

CDR2' as shown in

SEQ ID NO: 7:

```
                                            (SEQ ID NO: 7)
RAS;
``` and
CDR3' as shown in

SEQ ID NO: 8:

```
                                            (SEQ ID NO: 8)
QSNYNSGSSSSAAA
```

In another preferred embodiment, the light chain variable region has the amino acid sequence shown in SEQ ID NO: 10.

```
                                            (SEQ ID NO: 10)
DVVMTQTPASVEAPVGGTVTIKCQASQSVSGYCSWYQQKPGQPPKLLIY

RASTLESGVPSRFSGSGSGTDFTLTISDLECADAATYYCQSNYNSGSSS

SAAAFGGGTEVVVK
```

In the fourth aspect of the present invention, there is provided a light chain of an antibody having the light chain variable region according to the third aspect of the present invention and a light chain constant region.

In another preferred embodiment, the light chain constant region is of rabbit origin, mouse origin or human origin.

In the fifth aspect of the present invention, there is provided an antibody having:

(1) the heavy chain variable region according to the first aspect of the present invention; and/or
(2) the light chain variable region according to the third aspect of the present invention.

In another preferred embodiment, the antibody has: the heavy chain according to the second aspect of the present invention; and/or the light chain according to the fourth aspect of the present invention.

In another preferred embodiment, the antibody is an antibody specific against CD19 antibody.

In another preferred embodiment, the antibody comprises a single chain antibody (scFv), a Fab or (Fab')$_2$, fragment, a double-chain antibody, a monoclonal antibody, a chimeric antibody (such as a human rabbit chimeric antibody, a rabbit mouse chimeric antibody), a rabbit-derived antibody, a mouse-derived antibody, or a humanized antibody.

In another preferred embodiment, the equilibrium dissociation constant $K_D$ of the antibody with the scFv of the CD19 antibody is $\leq 1$ nM, more preferably, $K_D \leq 100$ pM, most preferably, $K_D \leq 50$ pM.

In another preferred embodiment, the CD19 antibody is a murine monoclonal antibody FMC63.

In another preferred embodiment, the scFv of the CD19 antibody is present on the cell membrane of CAR-T cells in the form of CAR.

In another preferred embodiment, the trade names of the CAR-T cells are Kymriah and Yescarta.

In the sixth aspect of the present invention, there is provided a recombinant protein having:
(i) the heavy chain variable region according to the first aspect of the invention, the heavy chain according to the second aspect of the invention, the light chain variable region according to the third aspect of the invention, the light chain according to the fourth aspect of the invention, or the antibody according to the fifth aspect of the invention; and
(ii) an optional tag sequence assisting expression and/or purification.

In another preferred embodiment, the tag sequence comprises a secretory peptide tag.

In another preferred embodiment, the tag sequence comprises a 6His tag and/or an Fc tag.

In another preferred embodiment, the recombinant protein is specific to CD19 antibody.

In the seventh aspect of the present invention, there is provided a polynucleotide encoding a polypeptide selected from the group consisting of:
(1) the heavy chain variable region according to the first aspect of the invention, the heavy chain according to the second aspect of the invention, the light chain variable region according to the third aspect of the invention, the light chain according to the fourth aspect of the invention, or the antibody according to the fifth aspect of the invention; or
(2) the recombinant protein according to the sixth aspect of the present invention.

In the eighth aspect of the present invention, there is provided a vector comprising the polynucleotide according to the seventh aspect of the present invention.

In another preferred embodiment, the vectors include bacterial plasmids, bacteriophages, yeast plasmids, plant cell viruses, mammalian cell viruses (such as adenoviruses, retroviruses, lentiviruses, etc.), transposons or other vectors.

In the ninth aspect of the present invention, there is provided a genetically engineered host cell comprising the vector according to the eighth aspect of the present invention or having the polynucleotide according to the seventh aspect of the present invention integrated in the genome.

In the tenth aspect of the present invention, there is provided an immunoconjugate comprising:
(a) the heavy chain variable region according to the first aspect of the invention, the heavy chain according to the second aspect of the invention, the light chain variable region according to the third aspect of the invention, the light chain according to the fourth aspect of the invention, or the antibody according to the fifth aspect of the invention; and
(b) a coupling moiety selected from the group consisting of a detectable label, a drug, a toxin, a cytokine, a radionuclide, an enzyme, a magnetic bead, agarose and the like.

In another preferred embodiment, the coupling moiety is selected from the group consisting of: a fluorescent or a luminescent label, a radioactive label, MRI (magnetic resonance imaging) or CT (electronic computer X-ray tomography technique) contrast agent, or an enzyme capable of producing detectable products, a radionuclide, a biotoxin, a gold nanoparticle/nanorod, a nanoparticle of any form, or a particle of any form in other size (e.g. a magnetic bead, an agarose particle), etc.

In the eleventh aspect of the present invention, there is provided a detection reagent for detecting CD19 CAR positive cells, comprising:
a first detection reagent which is the first antibody according to the fifth aspect of the present invention.

In another preferred embodiment, the detection reagent further comprises a second detection reagent specifically binding to the first antibody or a marker coupled to the first antibody.

In another preferred embodiment, the first antibody is a monoclonal antibody coupled to a fluorescent or luminescent label.

And the detection sensitivity of the detection reagent is ≥1 CD19 CAR positive cell/1000 cells.

In another preferred embodiment, the first antibody is an unmodified monoclonal antibody.

In another preferred embodiment, the second detection reagent is a second antibody specific to the first antibody.

In another preferred embodiment, the first antibody is a biotinylated monoclonal antibody and the second detection reagent is a streptavidin with a detectable label.

In another preferred embodiment, the detection sensitivity of the detection reagent is ≥1 CD19 CAR positive cells/1000 cells, more preferably ≥5 CD19 CAR positive cells/10000 cells, more preferably ≥1 CD19 CAR positive cells/10000 cells, more preferably ≥2 CD19 CAR positive cells/100000 cells.

In another preferred embodiment, the monoclonal antibody is a rabbit-derived monoclonal antibody.

In another preferred embodiment, the first antibody and the second antibody are from different mammalian species.

In another preferred embodiment, the first antibody is of rabbit origin and the second antibody is of donkey or sheep origin.

In another preferred embodiment, the CAR positive cells include CAR immune cells and CAR non-immune cells.

In another preferred embodiment, the CAR positive cells are selected from the group consisting of T cells, NK cells, CIK cells, NKT cells, and combinations thereof.

In another preferred embodiment, the CAR positive cells include HEK-293T cells, Jurkat cells, and combinations thereof.

In another preferred embodiment, the monoclonal antibody further has one or more of the following characteristics:
(i) binding to the CD19 CAR scFv recombinant protein with $EC_{50}$ of 0.3-3 nM, preferably 0.3-1 nM;
(ii) binding to the CD19 CAR scFv recombinant protein with an effective concentration of 0.02-0.2 μg/ml, preferably 0.02-0.1 μg/ml;
(iii) the equilibrium dissociation constant with the CD19 CAR scFv recombinant protein is $10^{-10}$-$10^{-12}$M.

In another preferred embodiment, the monoclonal antibody specifically recognizes and binds to CD19 CAR constructed based on scFv of anti-CD19 monoclonal antibody FMC63.

In another preferred embodiment, the extracellular antigen binding domain of the CD19 CAR has the amino acid sequence shown in

SEQ ID NO: 1:
(SEQ ID NO: 1)
DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLEITGGGGSGGGGSGGGGSEVKLQESGPGLVAPSQSLSVTCTVS

GVSLPDYGVSWIRQPPRKGLEWLGVIWGSETTYYNSALKSRLTIIKDNS

KSQVFLKMNSLQTDDTAIYYCAKHYYYGGSYAMDYWGQGTSVTVSS

In another preferred embodiment, the CD19 CAR scFv recombinant protein has a CD19 CAR scFv-His tag structure.

In another preferred embodiment, the CD19 CAR scFv recombinant protein has the amino acid sequence of

SEQ ID NO: 2:
(SEQ ID NO: 2)
DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLEITGGGGSGGGGSGGGGSEVKLQESGPGLVAPSQSLSVTCTVS

GVSLPDYGVSWIRQPPRKGLEWLGVIWGSETTYYNSALKSRLTIIKDNS

KSQVFLKMNSLQTDDTAIYYCAKHYYYGGSYAMDYWGQGTSVTVSSHHH

HHH .

In another preferred embodiment, the monoclonal antibody is prepared by the following method:
(a) providing CD19 CAR scFv recombinant proteins; and
(b) immunizing rabbits with the recombinant proteins to obtain antiserum against the CD19 CAR scFv recombinant protein; and
(c) carrying out monoclonal culture with peripheral blood B cells of the immunized rabbits, screening positive B cell monoclones, thereby obtaining rabbit B cell monoclones against the CD19 CAR scFv recombinant protein; and
(d) sequencing the positive rabbit B cell monoclone to obtain the light/heavy chain gene sequence of the monoclonal antibody; and
(e) using the light/heavy chain gene sequence of the monoclonal antibody to construct expression plasmids and transfecting eukaryotic host cells to obtain transfected eukaryotic host cells; and
(f) culturing the transfected eukaryotic host cells under conditions suitable for expression to express the monoclonal antibody; and (g) isolating and/or purifying the monoclonal antibody from the culture system.

In another preferred embodiment, the expression comprises secretory expression (i.e. secreted into the cell culture medium).

In another preferred embodiment, the eukaryotic host cells are selected from the group consisting of HEK-293T cells, CHO cells, COS-1 cells, and COS-7 cells.

In another preferred embodiment, the CD19 CAR scFv recombinant protein has the amino acid sequence of SEQ ID NO: 1 or 2.

In another preferred embodiment, the CD19 CAR scFv recombinant protein comprises a eukaryotic or prokaryotic expressed recombinant protein.

In another preferred embodiment, the CD19 CAR scFv recombinant protein is a recombinant protein expressed by *Escherichia coli*.

In another preferred embodiment, the CD19 CAR scFv recombinant protein is renatured.

In another preferred embodiment, the CD19 CAR scFv recombinant protein is eukaryotic expressed.

In another preferred embodiment, the CD19 CAR scFv recombinant protein is prepared by the following method:
(a) providing an expression plasmid comprising an expression cassette of the CD19 CAR scFv recombinant protein;
(b) transfecting the eukaryotic host cell with the expression plasmid, thereby obtaining the transfected eukaryotic host cell;
(c) culturing the transfected eukaryotic host cell under conditions suitable for expression, thereby expressing the recombinant protein; and
(d) isolating and/or purifying the recombinant protein from the culture system.

In another preferred embodiment, the expression comprises secretory expression (i.e. secreted into the cell culture medium).

In another preferred embodiment, the eukaryotic host cells are selected from the group consisting of HEK-293T cells, CHO cells, COS-1 cells, and COS-7 cells.

In the twelfth aspect of the present invention, there is provided a method for preparing a primary antibody which is a monoclonal antibody and which specifically binds to the extracellular antigen binding domain of CD19 CAR;
and the method comprises the following steps:
(a) providing CD19 CAR scFv recombinant proteins; and
(b) immunizing rabbits with the recombinant proteins to obtain antiserum against the CD19 CAR scFv recombinant protein; and
(c) carrying out monoclonal culture with peripheral blood B cells of the immunized rabbits, screening positive B cell monoclones, thereby obtaining rabbit B cell monoclones against the CD19 CAR scFv recombinant protein; and
(d) sequencing the positive rabbit B cell monoclone to obtain the light/heavy chain gene sequence of the monoclonal antibody; and
(e) using the light/heavy chain gene sequence of the monoclonal antibody to construct expression plasmids and transfecting eukaryotic host cells to obtain transfected eukaryotic host cells; and
(f) culturing the transfected eukaryotic host cells under conditions suitable for expression to express the monoclonal antibody; and
(g) isolating and/or purifying the monoclonal antibody from the culture system.

In another preferred embodiment, the expression comprises secretory expression (i.e. secreted into the cell culture medium).

In another preferred embodiment, the eukaryotic host cells are selected from the group consisting of HEK-293T cells, CHO cells, COS-1 cells, and COS-7 cells.

In another preferred embodiment, the CD19 CAR scFv recombinant protein has the amino acid sequence shown in SEQ ID NO: 1 or 2.

In another preferred embodiment, the method further comprises an optional step of
(h) optionally performing a performance assay on the isolated and/or purified monoclonal antibody.

In another preferred embodiment, the performance assay comprises one or more tests selected from the group consisting of:
(i) specificity detection;
(ii) titer detection;
(iii) sensitivity detection;
(vi) neutralization block detection;
(v) binding kinetics detection.

In another preferred embodiment, the first antibody is the antibody of the fifth aspect of the present invention.

In the thirteenth aspect of the present invention, there is provided a CD19 CAR detection kit comprising
(t1) a first container containing the monoclonal antibody according to the fifth aspect of the present invention, and the monoclonal antibody specifically binds to the extracellular antigen binding domain of CD19 CAR, and optional (t0) instructions.

In another preferred embodiment, the monoclonal antibody carries a detectable label.

In another preferred embodiment, the detectable label comprises a fluorescent or luminescent label.

In another preferred embodiment, the monoclonal antibody is a fluorescently labeled monoclonal antibody.

In another preferred embodiment, the detection kit further comprises (t2) a second container, containing a secondary antibody specific to the monoclonal antibody.

In another preferred embodiment, the first container and the second container may be integral or separate.

In another preferred embodiment, the second antibody is an antibody against rabbit IgG.

In another preferred embodiment, the second antibody is selected from the group consisting of a donkey anti-rabbit IgG antibody and a goat anti-rabbit IgG antibody.

In another preferred embodiment, the second antibody carries a detectable label.

In another preferred embodiment, the detectable label comprises a fluorescent or luminescent label.

In another preferred embodiment, the second antibody is a fluorescently labeled secondary antibody.

In another preferred embodiment, the detection kit further comprises one or more additional detection reagents selected from the group consisting of:
(t3) a third container, and a sealing agent within the third container; and
(t4) a fourth container, and a positive control (e.g. a CD19 CAR scFv recombinant protein) within the fourth container; and
(t5) a fifth container, and a negative control reagent within the fifth container.

In another preferred embodiment, the additional detection reagents are located in the same or different containers.

In another preferred embodiment, the instructions describe a method for detecting CD19 CAR positive cells.

In the fourteenth aspect of the present invention, there is provided a use of the detection reagent according to the eleventh aspect of the present invention for preparing a reagent or kit for detecting CD19 CAR positive cells.

In another preferred embodiment, the CAR positive cells include CAR immune cells and CAR non-immune cells.

In another preferred embodiment, the CAR positive cells are selected from the group consisting of T cells, NK cells, CIK cells, NKT cells, and combinations thereof.

In another preferred embodiment, the CAR positive cells include HEK-293T cells, Jurkat cells, and combinations thereof.

In the fifteenth aspect of the present invention, there is provided a method for detecting CD19 CAR positive cells, comprising the steps of:
(I) providing the detection reagent according to the eleventh aspect of the present invention;
(II) detecting a cell population to be tested with the detection reagent, thereby obtaining a qualitative or quantitative detection result of CD19 CAR positive cells.

In another preferred embodiment, the method comprises the steps of:
(1) taking $1\times10^5$-$1\times10^6$ cells to be tested, and washing 1-3 times with buffer containing blocking agent (such as PBS, containing 1% blocking agent);
(2) resuspending the cells with 50-200４ of a buffer containing blocking agent and monoclonal antibodies with detectable labels (e.g., PBS, containing 1% blocking agent, and 1-100 ng of the monoclonal antibody), and placing at 2-15° C. (preferably 4±2° C.) for a period of time T1 (e.g., 10-60 minutes, preferably about 15-45 minutes);
(3) washing the cells 1-3 times with buffer (e.g. PBS);
(4) resuspending the cells with a certain amount (such as 100-500４) of buffer (e.g. PBS) and detecting by flow cytometry.

In another preferred embodiment, the detectable label comprises a fluorescent or luminescent label.

In another preferred embodiment, the monoclonal antibody is a fluorescently labeled monoclonal antibody.

In another preferred embodiment, the method comprises the steps of:
(1) taking $1\times10^5$-$1\times10^6$ cells to be tested, and washing 1-3 times with buffer containing blocking agent (such as PBS, containing 1% blocking agent);
(2) resuspending the cells with 50-200４ of a buffer containing blocking agent and the first antibodies (monoclonal antibodies) (e.g., PBS, containing 1% blocking agent, and 1-100 ng of the monoclonal antibody such as R19mab), and placing at 2-15° C. (preferably 4±2° C.) for a period of time T1 (e.g., 10-60 minutes, preferably about 15-45 minutes);
(3) washing the cells 1-3 times with buffer (e.g. PBS);
(4) resuspending the cells with 50-200４ of a buffer containing the second antibodies with detectable labels (such as fluorescent groups) (e.g., PBS, containing 100-500 ng of the secondary antibody), and placing at 2-15° C. (preferably 4±2° C.) for a period of time T2 (e.g., 10-60 minutes, preferably about 15-30 minutes);
(5) washing the cells 1-3 times with buffer (e.g. PBS);
(6) resuspending the cells with a certain amount (such as 100-500４) of buffer (e.g. PBS) and detecting by flow cytometry.

In another preferred embodiment, the method is an in vitro detection method.

In another preferred embodiment, the method is a non-diagnostic and non-therapeutic method.

In another preferred embodiment, the method is a quality control method.

It should be understood that within the scope of the present invention, each technical features of the present invention described above and in the following (as examples) may be combined with each other to form a new or preferred technical solution, which is not listed here due to space limitations.

DESCRIPTION OF FIGURE

FIG. 5 shows the results of FMC63 scFv blocking the binding of R19mab to CD19 CAR-T. In which FIG. 5A shows the blocking effect of different concentrations of FMC63 scFv, and FIG. 5B shows the IC50 measurement results of the blocking effect of FMC63 scFv.

DETAILED DESCRIPTION

Figure 1:
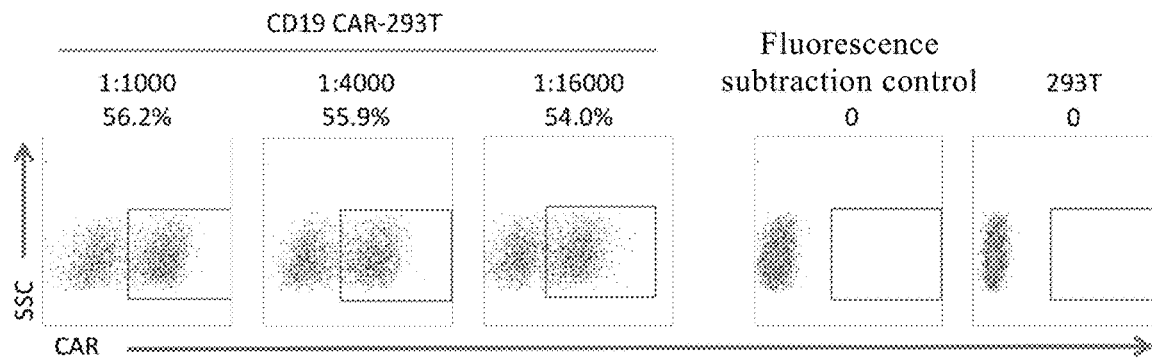
FIG. 1 shows the results of detecting the titer of CD19 CAR positive cells by rabbit antiserum of the present invention.

Through extensive and intensive research and a lot of screening, the inventors have unexpectedly obtained a monoclonal antibody R19mab against CD19 antibody. Experimental results show that the monoclonal antibody against CD19 antibody has high specificity and affinity. The present invention also provides a detection reagent with high sensitivity, good accuracy and good specificity for the detection of CAR-T cells. The detection method based on the detection reagent of the present invention can not only directly target the extracellular antigen binding region on CAR-T cells, but also has a detection sensitivity much higher than that of various existing detection reagents. In addition, the detection reagent of the present invention has a very high degree of discrimination between positive CAR-T cells and negative CAR-T cells, and the detection result is more accurate. The present invention has been completed on this basis.

Term

As used herein, the term "antibody" or "immunoglobulin" is a heterotetrameric glycoprotein of about 150,000 Da having the same structural characteristics, which consists of two identical light chains (L) and two identical heavy chains (H). Each light chain is linked to a heavy chain via a covalent disulfide bond, and different immunoglobulin isotypes have different numbers of disulfide bonds between the heavy chains. There are also regularly spaced intrachain disulfide bonds in each heavy and each light chain. Each heavy chain has a variable region (VH) at one end, followed by a plurality of constant regions. Each light chain has a variable region (VL) at one end and a constant region at the other end; the constant region of light chain pairs with the first constant region of heavy chain, and the variable region of light chain pairs with the variable region of heavy chain. Special amino acid residues form an interface between the variable regions of a light chain and a heavy chain.

As used herein, the term "variable" means that certain portion of the variable region in an antibody differ in sequence, which is responsible for the binding and specificity of various specific antibodies to their specific antigen. However, the variability is not distributed evenly throughout the variable regions of an antibody. It is concentrated in three fragments called complementarity determination regions (CDRs) or hypervariable regions in light chain and heavy chain variable regions. The conserved parts of variable regions are called framework regions (FRs). Each of the variable regions of naturally occurring heavy and light chains comprises four FR regions, which are generally in a β-sheet configuration, joined by the three CDRs forming a linking loop, and in some cases, may form a partial β-sheet structure. The CDRs in each chain are closely linked together via the FR regions, and together with the CDRs of the other chain, form the antigen binding site of an antibody (see Kabat et al., NIH Publ. No. 91-3242, Volume I, pages 647-669 (1991)). Constant regions are not directly involved in the binding of antibodies to antigen, however, they exhibit different effector functions, such as participating in the antibody-dependent cytotoxicity of antibodies.

As used herein, the term "monoclonal antibody (mAb)" refers to an antibody obtained from a substantially homogeneous population, i.e., the individual antibodies contained in the population are the same, except for a few naturally occurring mutations that may be present. A monoclonal antibody is highly specific for a single antigenic site. Moreover, unlike conventional polyclonal antibody preparations (usually with different antibodies directed against different determinants), each monoclonal antibody is directed against a single determinant on the antigen. In addition to their specificity, the advantage of monoclonal antibodies is that they can be synthesized by recombinant expression of eukaryotic cells and will not be contaminated by other immunoglobulins. The modifier "monoclonal" indicates the characteristics of antibodies, which are obtained from a substantially uniform antibody population, which should not be interpreted as requiring any special method to produce antibodies.

The present invention includes not only complete monoclonal antibodies, but also antibody fragments with immune activity, such as single chain antibodies; Fab or Fab'$_2$ fragments; antibody heavy chains; antibody light chains.

As used herein, the terms "heavy chain variable region" and "$V_H$" can be used interchangeably.

As used herein, the terms "variable region" and "complementarity determine region (CDR)" can be used interchangeably.

In a preferred embodiment of the present invention, the heavy chain variable region of the antibody comprises the following three complementarity determining regions or CDRs:

CDR1, whose amino acid sequence is (SEQ ID NO: 3)
GIDFRNYG;

CDR2, whose amino acid sequence is (SEQ ID NO: 4)
FSSSGST;

CDR3, whose amino acid sequence is (SEQ ID NO: 5)
ARHPGPTNGWKL.

In another preferred embodiment, the amino acid sequence of the heavy chain variable region is:

(SEQ ID NO: 9)
QSLEESGGRLVTPGTPLTLTCTVSGIDFRNYGVSWVRQAPGKGLEWIGI
FSSSGSTYYATWAKGRFTISKASSTTVDLKMTSLTTEDTATYFCARHPG
PTNGWKLWGPGTLVTVSS.

In a preferred embodiment of the present invention, the heavy chain of the antibody comprises the aforementioned heavy chain variable region and a heavy chain constant region, which may be of rabbit origin, mouse origin or human origin.

As used herein, the terms "light chain variable region" and "$V_L$" can be used interchangeably.

In a preferred embodiment of the invention, the light chain variable region of the antibody according to the invention has complementarity determining regions CDR selected from the group consisting of:

CDR1', whose amino acid sequence is (SEQ ID NO: 6)
QSVSGY;

CDR2', whose amino acid sequence is (SEQ ID NO: 7)
RAS;

CDR3', whose amino acid sequence is (SEQ ID NO: 8)
QSNYNSGSSSAAA.

In another preferred embodiment, the amino acid sequence of the light chain variable region is:

(SEQ ID NO: 10)
DVVMTQTPASVEAPVGGTVTIKCQASQSVSGYCSWYQQKPGQPPKLLIY

RASTLESGVPSRFSGSGSGTDFTLTISDLECADAATYYCQSNYNSGSSS

SAAAFGGGTEVVVK.

The invention also provides other proteins or fusion expression products having antibodies of the invention. Specifically, the present invention includes any protein or protein conjugate and fusion expression product (i.e., immunoconjugate and fusion expression product) having a heavy chain and a light chain containing variable regions, as long as the variable region is the same as or has at least 90% homology with the variable regions of the heavy chain and light chain of the antibody of the present invention, preferably at least 95% homology.

As used herein, the term "CAR" refers to the chimeric antigen receptor, comprising an extracellular domain, a transmembrane domain, and an intracellular domain. The extracellular domain includes a target-specific binding element (also called antigen binding domain). The intracellular domain includes a costimulatory signal transduction region and a zeta chain part. The costimulatory signal transduction region refers to a part of intracellular domain including costimulatory molecules. The costimulatory molecules are cell surface molecules needed by lymphocytes to effectively respond to antigens.

Kit

The present invention also provides a detection kit for detecting CD19 CAR. The detection kit (direct labeling method) comprises:
- (t1) a first container, and monoclonal antibodies with detectable labels within the first container, and the monoclonal antibody specifically binds to the extracellular antigen binding domain of CD19 CAR.
- (t0) instructions.

In another preferred embodiment, the detectable label comprises a fluorescent or luminescent label.

In another preferred embodiment, the monoclonal antibody is a fluorescently labeled monoclonal antibody.

In another preferred embodiment, the detection kit (secondary antibody method) comprises:
- (t1) a first container, and a first antibody within the first container, wherein the first antibody is a monoclonal antibody specifically binding to the extracellular antigen binding domain of CD19 CAR; and
- (t2) a second container, and a second antibody within the second container that is specific to the monoclonal antibody; and
- (t0) instructions.

In another preferred embodiment, the second antibody is an antibody against rabbit IgG.

In another preferred embodiment, the second antibody is selected from the group consisting of a donkey anti-rabbit IgG antibody and a goat anti-rabbit IgG antibody.

In another preferred embodiment, the second antibody carries a detectable label.

In another preferred embodiment, the detectable label comprises a fluorescent or luminescent label.

In another preferred embodiment, the second antibody is a fluorescently labeled secondary antibody.

In another preferred embodiment, the detection kit further comprises one or more additional detection reagents selected from the group consisting of:
- (t3) a third container, and a sealing agent within the third container; and
- (t4) a fourth container, and a positive control (e.g. a CD19 CAR scFv recombinant protein) within the fourth container; and
- (t5) a fifth container, and a negative control reagent within the fifth container.

In another preferred embodiment, the additional detection reagents are located in the same or different containers.

In another preferred embodiment, the instructions describe a method for detecting CD19 CAR positive cells.

Detection Method

The present invention also provides a method for detecting CAR positive cells based on the monoclonal antibody of the invention. Since the monoclonal antibody of the present invention has high affinity and high specificity for the antigen binding region of matched or corresponding CAR, the monoclonal antibody of the present invention can be used to efficiently, sensitively and accurately detect CAR positive cells.

For the CAR positive cells that can be detected by the method of the present invention, representative examples include, but are not limited to: T cells, NK cells, NKT cells, CIK cells and many other different cells. For example, taking the rabbit monoclonal antibody (R19 mab) against FMC63 scFv of the present invention as an example, it can be used for the detection of corresponding CD19 CAR positive cells (including T, NK, NKT or CIK cells).

The detection method of the present invention can be used in scientific research, research and development of cell drugs, quality control of cell drugs, clinical treatment monitoring of cell drugs, auxiliary diagnosis of clinical patients and the like.

The Main Advantages of the Present Invention Include:
- (a) The equilibrium dissociation constant $K_D$ value of the rabbit monoclonal antibody R19mab of the present invention binding to the FMC63 scFv reaches 43 pM, and the detection sensitivity of R19mab determined by flow cytometry reaches 1:10000. Therefore, the detection kit for CAR positive cells developed based on the monoclonal antibody of the present invention has high detection sensitivity and good specificity.
- (b) The detection reagent and method of the present invention have a very high degree of discrimination between CAR positive cells and CAR negative cells, and the detection results are more accurate.
- (c) The rabbit monoclonal antibody of the present invention has a high affinity to mouse FMC63 (significantly better than the affinity of mouse monoclonal antibody to mouse FMC63).
- (d) Compared with existing detection reagents such as anti-mouse IgG (Fab')$_2$, Protein L, CD19/Fc, GFP-CD19, mouse monoclonal antibody 136.20.1, the rabbit monoclonal antibody of the present invention can detect CD19 CAR positive cells more specifically, sensitively and accurately, and meet the requirements of CAR-T drug production quality control, clinical treatment monitoring and auxiliary diagnosis.
- (e) The production cost of the rabbit monoclonal antibody and the kit of the present invention is significantly reduced, so it is more advantageous to be applied to CAR-T drug quality control, clinical treatment monitoring and auxiliary diagnosis.

The present invention is further explained below in conjunction with specific example. It should be understood that these examples are only for illustrating the present invention and not intend to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions recommended by the manufacturer. Unless otherwise stated, percentages and parts are percentages by weight and parts by weight.

General Methods

1. T Cell Activation and CD19 CAR Lentivirus Infection
   - (1) $0.5 \times 10^6$ T cells ($0.5 \times 10^6$/mL) were taken, and placed in a 24-well plate.
   - (2) The magnetic beads coated with anti-CD3/CD28 were washed with R10 culture medium 3 times according to the instructions.

(3) Magnetic beads were added to T cells at a ratio of 3:1 (magnetic beads: cells), and placed in an incubator at 37° C., 5% CO2 overnight.
(4) After activating T cells for 12-24 hours, the 24-well plate was centrifuged to remove 800 μL supernatant culture medium.
(5) Lentivirus particles were thawed at room temperature, and mixed gently. 1 mL lentivirus particles was added into $0.5 \times 10^6$ T cells (200 L), and polybrene was added to a final concentration of 8 g/mL, then placed in a centrifuge at 2500 rpm for 1.5 hours, and placed in an incubator after centrifugation at 37° C., 5% CO2 overnight.
(6) The 24-well plate cultured overnight was centrifuged to remove most supernatant culture medium containing lentivirus particles. Fresh R10 culture medium was added to expand T cells.
(7) T cells were counted every 2 days, and IL-2 50 IU/mL was added to maintain T cells at $0.5\text{-}1 \times 10^6$/ml.
(8) After 3-5 days, $2 \times 10^5$ cells were taken to detect CD19 CAR-T cells by flow cytometry.

2. Detection of CD19 CAR-T Cells by Flow Cytometry (Secondary Antibody Method)
(1) $2 \times 10^5$ CD19 CAR-T cells were taken, washed twice with PBS and resuspended with 100 μL PBS.
(2) Detection antibodies (or other detection reagents) with corresponding dilution ratio were added, and placed at 4° C. for 45 minutes.
(3) Washed twice with PBS.
(4) Fluorescent secondary antibody was added, and placed at 4° C. in the dark for 30 minutes.
(5) Washed with PBS twice.
(6) Resuspended with 200 μL PBS and detected by flow cytometry.

3. Detection of CD19 CAR-T Cells by Flow Cytometry (Direct Labeling Method)
(1) $2 \times 10^5$ CD19 CAR-T cells were taken, washed twice with PBS and resuspended with 100 μL PBS.
(2) Fluorescent labeled detection antibodies (or other detection reagents) with corresponding dilution ratio were added, and placed at 4° C. for 45 minutes.
(3) Washed twice with PBS.
(4) Resuspended with 200 μL PBS and detected by flow cytometry.

Example 1. Preparation Method of Rabbit Monoclonal Antibody (R19mab) Against FMC63 scFv (1) Preparation and Purification of Recombinant Antigen An expression plasmid containing the FMC63 scFv-His tag recombinant antigen sequence (amino acid sequence as shown in SEQ ID NO: 2) was constructed. 293T cells were cultured in a 10 cm culture dish. According to the instructions of lipofectamine, the expression plasmid containing the recombinant antigen sequence of FMC63 scFv-His tag was transfected into 293T cells. The culture medium was harvested on the sixth day after transfection, and the cells were removed by centrifugation to obtain supernatant. The recombinant antigen in the supernatant was purified according to the instructions of Ni-NTA Superflow of QIAGEN Company.

Results: After purification, the antigen concentration was 0.5-4 mg/ml.

(2) Immunization of Rabbits with Recombinant Antigen

The purified recombinant protein was used as antigen to immunize rabbits. In short, 0.5 mL of Freund's complete adjuvant was fully mixed with 0.5 mL of antigen (200 μg). Each rabbit was immunized 4 parts (both the back and thigh root), and each part was 0.25 mL. The immunization cycle was 20 days, and blood was taken 7-10 days after immunization to detect antiserum titer. A total of 4-5 immunizations were conducted.

(3) Detection of CD19 CAR Positive Cell Titer by Rabbit Antiserum

The lentiviral plasmid containing FMC63 scFv CD19 CAR sequence and the lentiviral plasmid containing BCMA CAR sequence were mixed with three packaging plasmids VSVg, gag/pol, rev, respectively, and 293T cells were transfected with lipofectamine reagent. 24 and 48 hours after transfection, cell supernatant was collected, filtered and ultracentrifuged to obtain purified CD19 CAR lentivirus and BCMA CAR lentivirus, and stored at −80° C. CD19 CAR-293T cells were obtained by infecting 293T cells with CD19 CAR lentivirus. Rabbit antiserum was gradient diluted with cold FACS buffer. $2 \times 10^5$ CD19 CAR-293T cells were suspended in 50 μL FACS buffer. 50 μL dilute solution of antiserum was then added to 50 μL cell suspension and the mixture was incubated on ice for 30 minute. The cells were then washed twice with cold FACS buffer. Goat anti-rabbit IgG (H+L)-Alexa Fluor 647 secondary antibody (Table 1) was added and the mixture was incubated on ice for 30 minutes, then the cells were washed twice with cold FACS buffer. The cells were resuspended in 200 pit FACS buffer and detected by flow cytometry.

Results:

As shown in FIG. 1, rabbit antiserum diluted at 1:16000 can detect CD19 CAR positive cells normally, indicating that the titer has reached at least ≥1:16000. The recombinant antigen prepared in Example 1 (1) can efficiently produce specific anti-FMC63 scFv antibodies in rabbits.

(4) Monoclonal Screening of Rabbit B Cells

Rabbit B cell monoclone expressing anti-FMC63 scFv antibodies was screened using the method of Stefan Seeber et al. (Stefan Seeber, et al., PLoS ONE, 2014). In short, peripheral blood of rabbits producing anti-FMC63 scFv antibodies was taken and peripheral blood mononuclear cells were isolated. FMC63 scFv recombinant protein was used to enrich positive B cell monoclones, and then B cell monoclones were cultured in 96-well plates. After 7 days, the B cell culture supernatant was taken, and flow cytometry test was performed according to the same protocol described in Example 1 (3), to identify rabbit B cell positive clones expressing anti-FMC63 scFv antibody. The positive clones were lysed and the heavy/light chain genes were obtained by RT-PCR. The heavy/light chain gene expression vector was constructed and transfected into 293T cells for expression. After 7 days, the cell culture supernatant was taken, and flow cytometry test was performed according to the same protocol described in Example 1 (3), to confirm the monoclonal antibody against FMC63 scFv, and then the heavy/light chain gene sequence of the antibody was obtained by sequencing.

Figure 2:
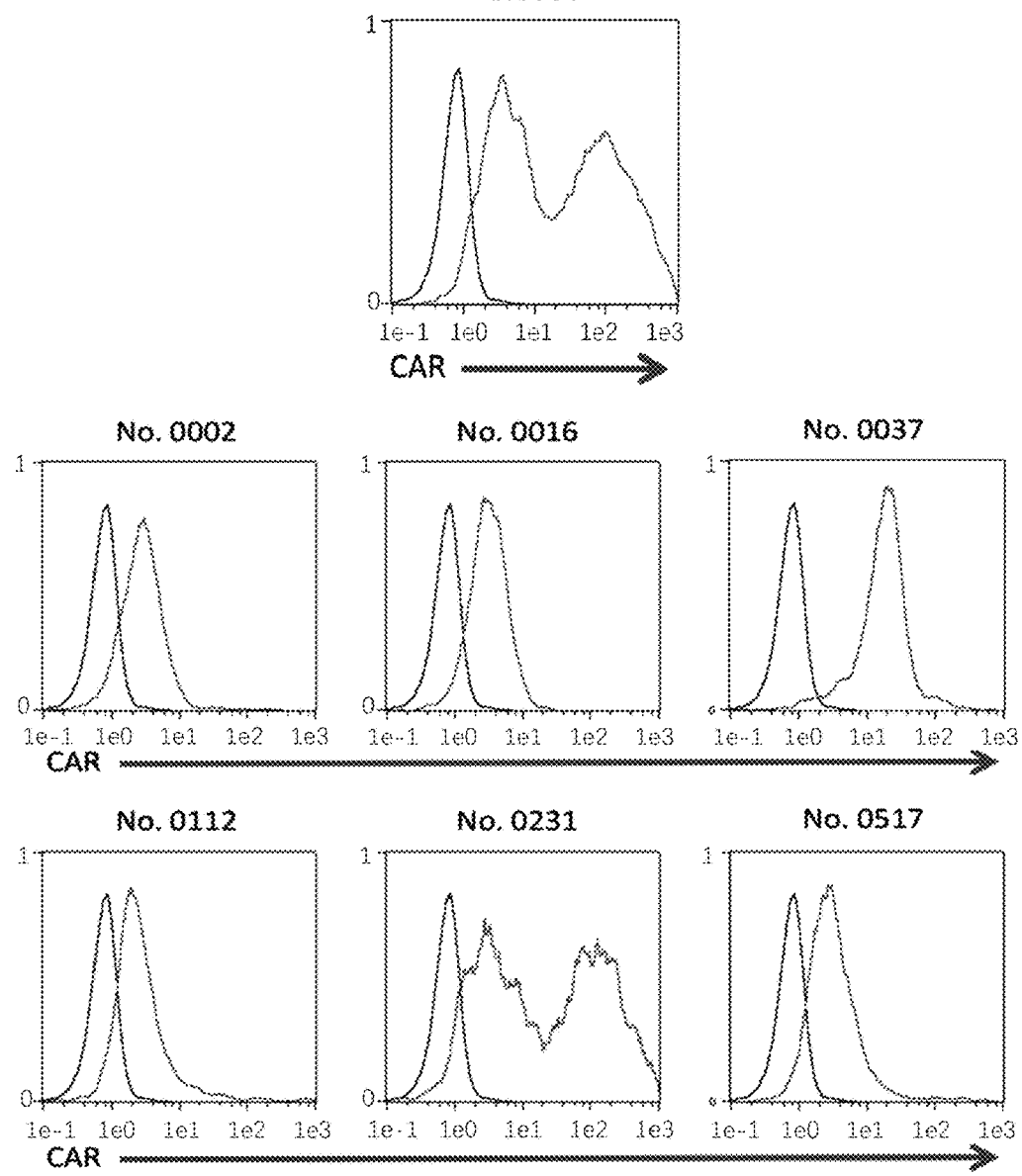
FIG. 2 shows the results of detecting CD19 CAR positive cells by rabbit B cell monoclonal culture supernatant.

Results:

As shown in FIG. 2, the B cell culture supernatant was screen by flow cytometry assay to confirm that No. 0231 was a rabbit B cell positive clone expressing anti-FMC63 scFv antibody. The heavy/light chain gene sequence of the antibody was obtained by sequencing, and the antibody was R19mab.

(5) Purification of Rabbit Monoclonal Antibody R19mab

The culture supernatant of 293T cells expressing R19mab was loaded into Protein-A chromatography column at a flow rate of about 1 mL/min, 20 mL equilibrium buffer (20 mM Na$_2$HPO$_4$, 0.15 M NaCl, pH 7.0) was used to wash resin at a flow rate of about 2 mL/min. The antibody was eluted with 10 mL elution buffer (0.1 M Glycine, pH 3.0) at a flow rate of about 1 mL/min, the elution was collected, and a neutralization buffer (1 M Tris, pH 8.5) of 1/10 volume of the elution buffer was immediately added to adjust the pH to 7.4. Concentrated to 1-1.5 mL with ultrafiltration tube, and then the antibody concentration was determined by spectrophotometer.

Results: After purification, the concentration of R19mab antibody was 0.5-4 mg/ml.

Example 2. Structural Characterization of R19mab

R19mab comprises a heavy chain variable region and a light chain variable region, wherein the complementarity determining region of the heavy chain variable region comprises the amino acid sequence of CDR1 as shown in SEQ IDNO: 3, the amino acid sequence of CDR2 as shown in SEQ ID NO: 4 and the amino acid sequence of CDR3 as shown in SEQ ID NO: 5, and the complementarity determining region of the light chain variable region comprises the amino acid sequence of CDR1' as shown in SEQ ID NO: 6, the amino acid sequence of CDR2' as shown in SEQ ID NO: 7 and the amino acid sequence of CDR3' as shown in SEQ ID NO: 8.

Example 3. Characterization of Binding Properties of R19mab

In this example, the binding of R19mab to FMC63 and FMC63 scFv was detected by ELISA. The binding of R19mab to CD19 CAR on the cell surface was detected by flow cytometry and immunofluorescence. The binding kinetics of R19mab to FMC63 scFv was analyzed by Fortebio Octet.

(1) ELISA Analysis

The binding specificity of R19mab to FMC63 and FMC63 scFv was detected by ELISA. The method is as follows:

96-well titer plates were coated with PBS containing 1 μg/ml of purified FMC63 scFv recombinant protein, FMC63 antibody or murine IgG at 100 pit per well (100 ng was coated), and incubated overnight at 4° C. Blocking was then performed with PBST (PBS containing 0.05% Tween 20) containing 5% BSA at 300 μL per well. Different concentrations of R19mab (0.022-5.625 μg/ml) were added to each well and incubated at ambient temperature for 1 hour. The plate was washed with PBST and then incubated at room temperature for 30 minutes with goat anti-rabbit IgG polyclonal antibody coupled with horseradish peroxidase (HRP). After washing, the plate was developed with an ABTS substrate and analyzed by spectrophotometer at OD 405.

Figure 3:
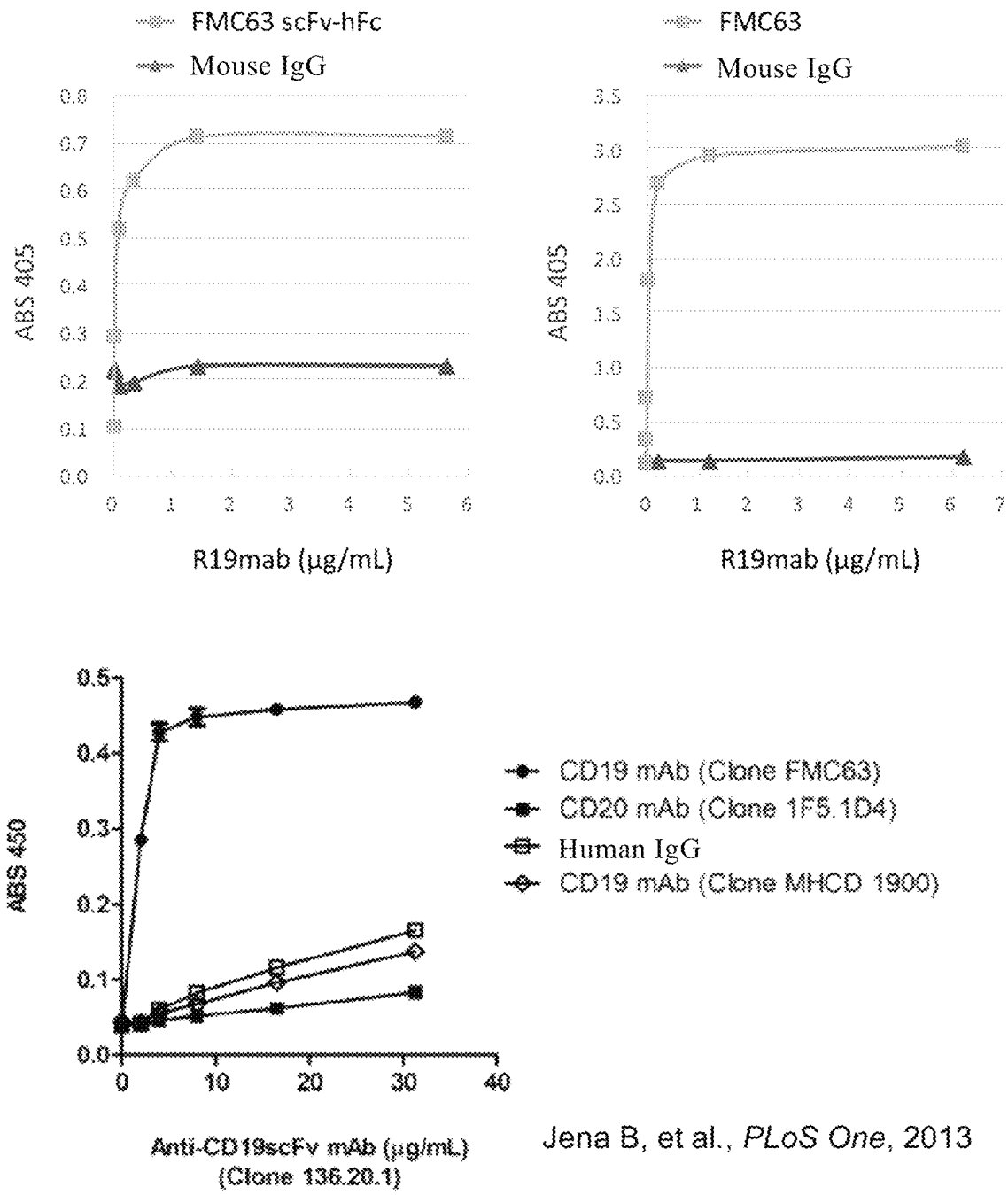
FIG. 3 shows the ELISA results of the rabbit monoclonal antibody R19mab of the present invention binding to FMC63 scFv and FMC63, compared with the data of mouse monoclonal antibody 136.20.1.

Results:

As shown in FIG. 3, the result of ELISA showed that R19mab bound to FMC63 scFv and FMC63 antibody, but did not bind to murine IgG, indicating that R19mab specifically recognized FMC63 scFv and FMC63 antibody and did not cross-react to other murine IgG. R19mab binds to FMC63 scFv with an EC$_{50}$ of 0.307 nM. The effective binding concentration is 0.022 μg/mL, and the saturated binding concentration is 0.352 μg/mL. R19mab binds to FMC63 with an EC$_{50}$ of 0.253 nM. The effective binding concentration is 0.002 μg/mL, and the saturated binding concentration is 0.25 μg/mL. The effective binding concentration of the murine monoclonal antibody 136.20.1 invented by Cooper et al. for binding to FMC63 is 2 μg/mL, and the saturated binding concentration is 4 μg/mL. Compared with 136.20.1, R19mab has significant advantages.

Therefore, under similar conditions, the effective binding concentration of the antibody of the present invention can be as low as 0.002 μg/mL, while the effective binding concentration of the existing antibody is 2 μg/mL, and the difference between the two is about 1000 times. In addition, the saturated binding concentration of the antibody of the present invention is 0.25 μg/mL, which is about 125 times of the effective binding concentration, while the saturated binding concentration of the existing antibody is only 2 times of the effective binding concentration. Therefore, the detection range of the antibody of the present invention is large, thereby saving costs.

(2) Flow Cytometry Research (I) CD19 CAR-T Cell Binding

T cells were infected with CD19 CAR lentivirus or BCMA CAR lentivirus to obtain corresponding CAR-T cells. R19mab, Protein L and isotype control (Rabbit IgG) antibody (Table 1) were diluted into 50 μL precooled FACS buffer. 2×10$^5$ cells were suspended in 50 μL FACS buffer. 50 μL antibody solution was then added to 50 μL cell suspension and the mixture was incubated on ice for 30 minutes. The cells were then washed twice with cold FACS buffer. The corresponding secondary antibody (R19mab, Rabbit IgG/Goat anti-Rabbit IgG (H+L), Alexa Fluor 488; Protein L/Streptavidin, FITC) was added. Table 1) and the mixture was incubated on ice for 30 minutes, after that the cells were washed twice with cold FACS buffer. The cells were resuspended in 200 μL FACS buffer and detected by flow cytometry.

Figure 4:
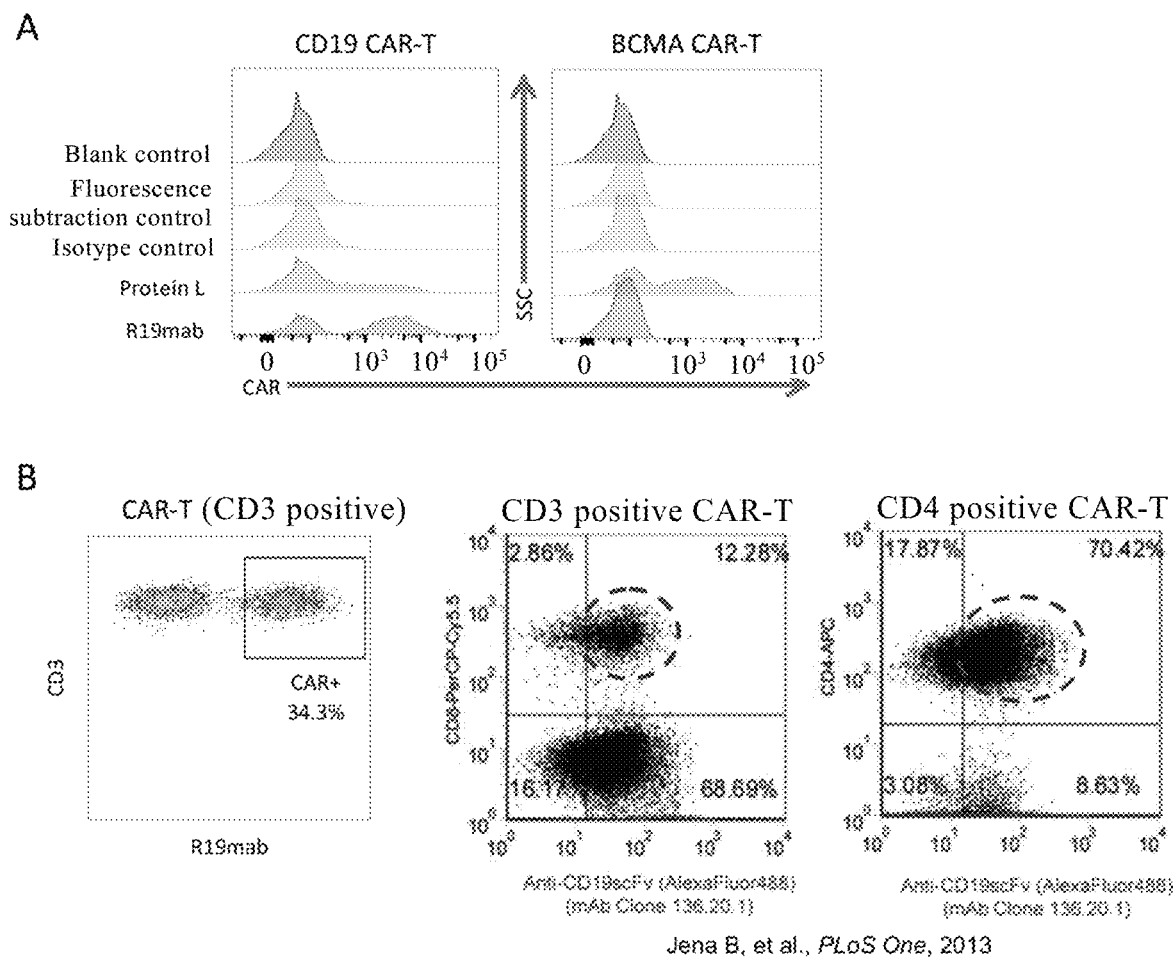
FIG. 4 shows the results of the detection of different target CAR-T (CD19 CAR-T and BCMA CAR-T) cells by the rabbit monoclonal antibody R19mab of the present invention.

Results:

As shown in FIG. 4A, R19mab recognizes the CD19 CAR structure on the cell surface, but not the BCMA CAR structure. The difference between the two is only in the scFv part. Therefore, R19mab specifically recognizes CD19 CAR positive cells containing FMC63 scFv sequences. On the contrary, Protein L cannot distinguish CD19 CAR from BCMA CAR, and the detection is not specific. In addition, R19mab can clearly distinguish CD19 CAR positive and negative cell groups, and the signal peaks of the two do not overlap. However, the negative signal and positive signal of Protein L detection results partially overlap, which makes it impossible to clearly distinguish positive and negative cell groups, and the detection accuracy is low.

As shown in FIG. 4B, when CD19 CAR-T cells are detected by R19mab, the positive signal (box) is completely separate from the negative signal. When CD19 CAR-T cells are detected by mouse monoclonal antibody 136.20.1 invented by Cooper et al., neither CD4 positive nor CD8 positive CAR-T (box) can be completely separated from negative T cells.

Therefore, the rabbit monoclonal antibody R19mab of the present invention is far superior to Protein L and mouse monoclonal antibody 136.20.1 in terms of detection specificity and accuracy.

In addition, combined with the detection method specific for CD4 and/or CD8, the method of the present invention can further effectively distinguish two subsets of CAR-positive CD4-positive T cells and CD8-positive T cells.

Because R19mab has high specificity and accuracy, and can clearly distinguish CD19 CAR positive and negative cell groups, CD19 CAR positive cells can be counted conveniently and accurately, which is very important for quality control of CD19 CAR-T drug production and auxiliary diagnosis of clinical treatment.

(II) FMC63 scFv Blocking R19mab Binding to CD19 CAR-T

The purified FMC63 scFv recombinant protein was gradient diluted with 1×PBS, R19mab (final concentration was 0.1 μg/mL) was added to the diluent, and incubated on ice for 30 minutes. $2×10^5$ CD19 CAR-T cells were suspended in 100 μL FACS buffer. A mixed solution of FMC63 scFv/R19mab was then added to the cell suspension, and a flow cytometry experiment was performed according to the same protocol described in Example 3 (2) (I) to analyze the blocking effect of FMC63 scFv on R19mab binding to CD19 CAR-T.

Figure 5:
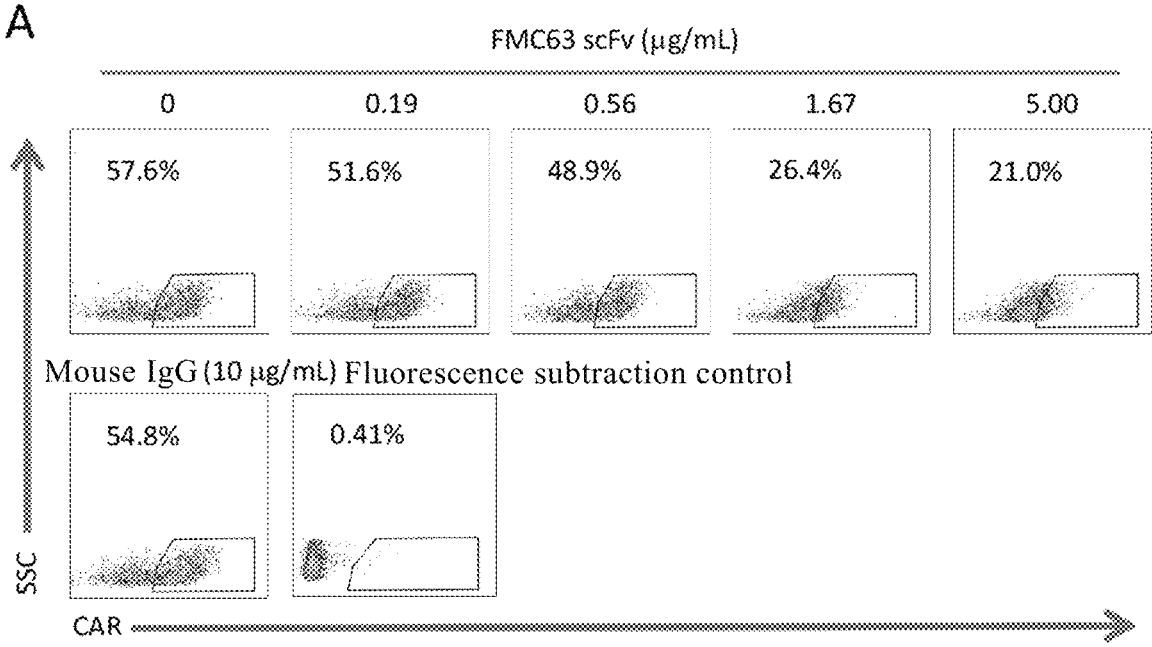
Figure 5:
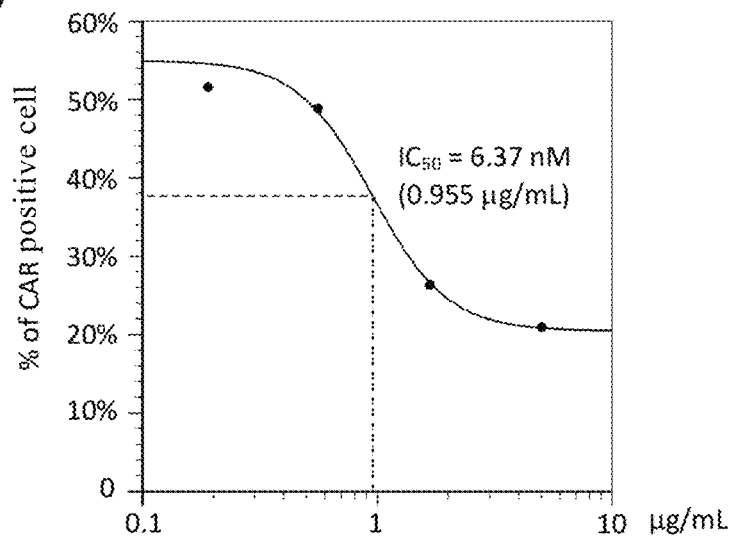

Results:

As shown in FIG. 5, FMC63 scFv effectively block the binding of R19mab to CD19 CAR-T (FIG. 5A), with an $IC_{50}$ of 6.37 nM (0.955 μg/mL) (FIG. 5B). The results indicate that R19mab specifically recognizes FMC63 scFv fragment on CD19 CAR.

(III) CD19 CAR-293T Cell Binding

CD19 CAR-293T cells were obtained by infecting 293T cells with CD19 CAR lentivirus. R19mab was gradient diluted with cold FACS buffer. $2×10^5$ CD19 CAR-293T cells were suspended in 50 μL FACS buffer. Then 50 μL R19mab antibody solution was added to 50 μL cell suspension, and flow cytometry was performed according to the same protocol described above to analyze R19mab binding.

Figure 6:
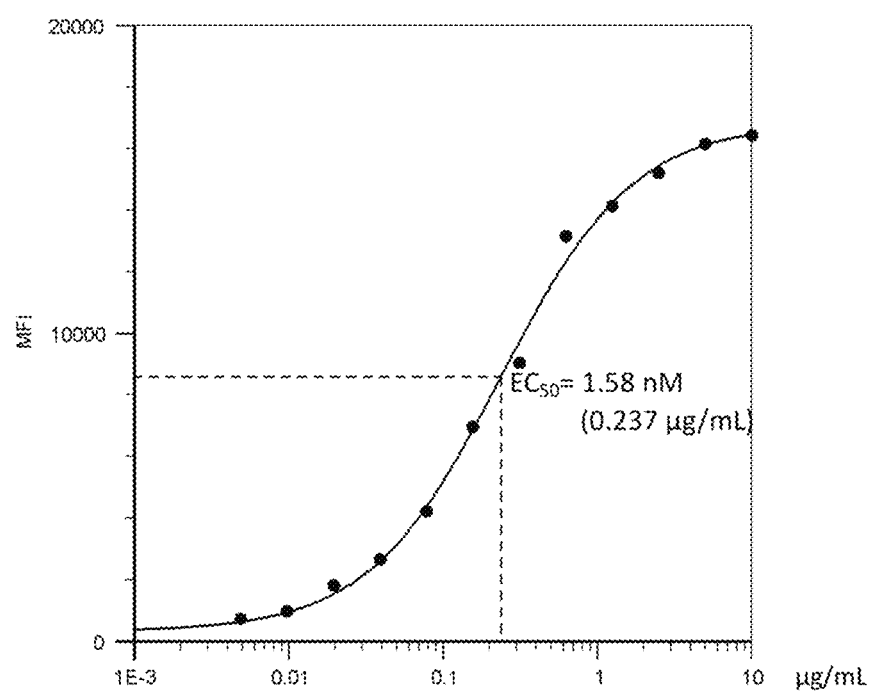
FIG. 6 shows the $EC_{50}$ measurement results of R19mab binding to CD19 CAR scFv on the cell surface.

Results:

As shown in FIG. 6, R19mab effectively binds to CD19 CAR scFv on the cell surface, with an $EC_{50}$ of 1.58 nM.

(IV) Sensitivity Analysis of R19mab Detection

CD19 CAR-T cells were mixed with different numbers of PBMC cells to reach CAR-T: PBMC cell ratios ranging from 1:10 to 1:10,000. Flow cytometry assays were performed according to the same protocol described in Example 1 (3) to analyze the sensitivity of R19mab in detecting CD19 CAR positive cells.

Figure 7:
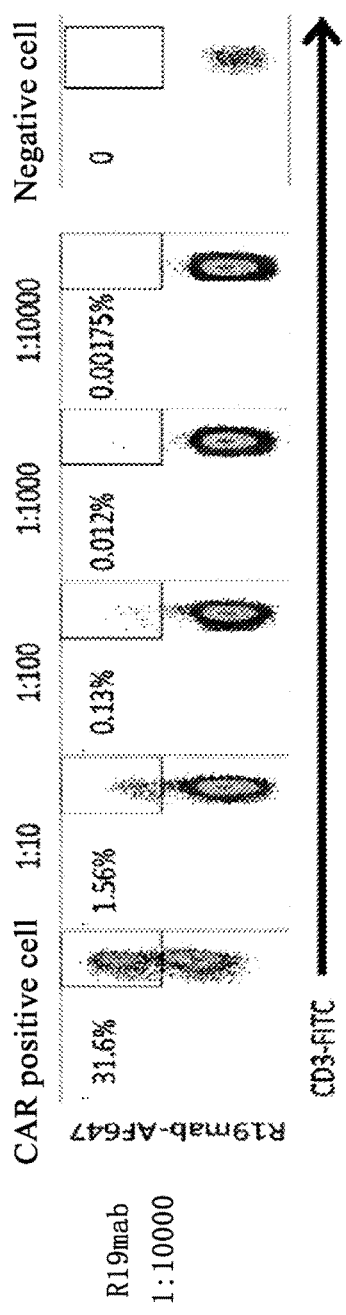
FIG. 7 shows the results of the sensitivity assay of R19mab binding to CD19 CAR positive cells, compared with the data of mouse monoclonal antibody 136.20.1 and the data of CD19/Fc.
Figure 7:
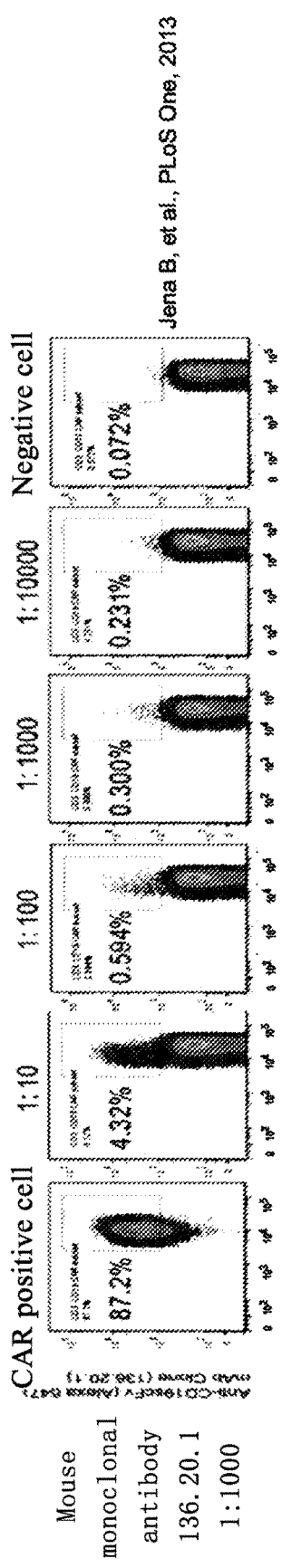
Figure 7:
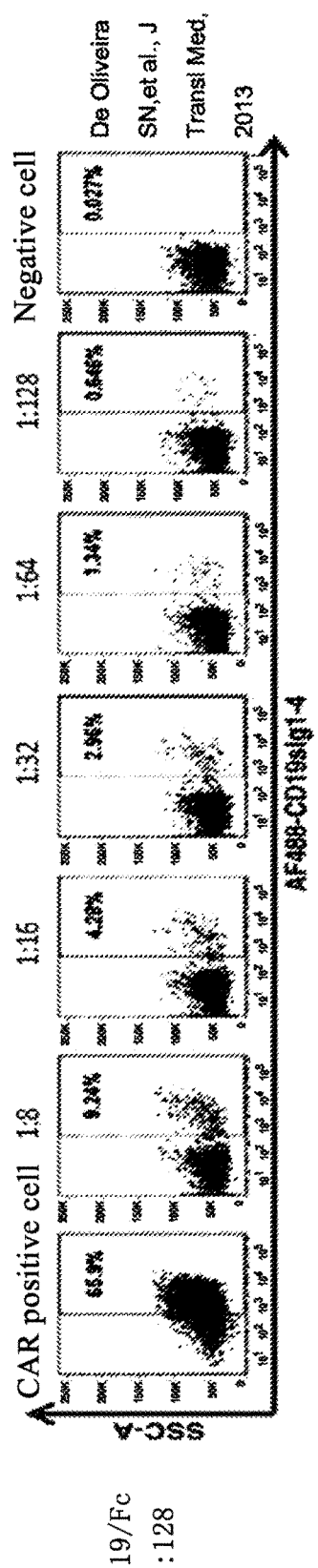

Results:

As shown in FIG. 7, two CD19 CAR positive cell out of 100,000 negative cells were detected using R19mab, with a detection sensitivity of 0.002%. The murine monoclonal antibody 136.20.1 invented by Cooper et al. has a detection sensitivity of 0.1% (Bipulendu Jena, et al., *PLoS One*, 2013), and the detection sensitivity of CD19/Fc (the number in the article is AF488-CD19sIg1-4) reaches 0.5% (Satiro N De Oliveira, et al., *Journal of Translational Medicine*, 2013). Therefore, in terms of detection sensitivity, R19mab is far superior to murine monoclonal antibodies 136.20.1 and CD19/Fc. Because R19mab has high sensitivity, it can conveniently and accurately count low abundance CD19 CAR positive cells, which is very important for detecting CD19 CAR-T cells in vivo, monitoring clinical treatment and auxiliary diagnosis.

(3) Immunofluorescence Detection

CD19 CAR-T cell were washed with 1×PBS and then fixed in 4% paraformaldehyde at room temperature for 20 mins. The cells were washed with 1×PBS followed by incubation with a blocking solution (PBS containing 10% donkey serum) at room temperature for 30 minutes. Cells were washed with 1×PBS and incubated with R19mab for 1 hour. After washing with 1×PBS, incubation was performed with goat anti-rabbit IgG (H+L)-Cy3 secondary antibody for 30 minutes. After smearing, the cells were observed and photographed with confocal microscope.

Figure 8:
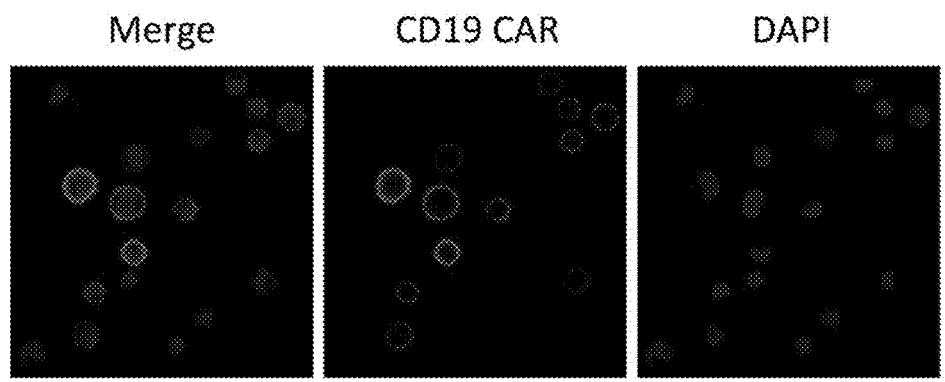
FIG. 8 shows the results of immunofluorescence assay of R19mab binding to CD19 CAR scFv on the cell surface.

Results:

As shown in FIG. 8, R19mab can clearly stain CD19 CAR positive T cells, and the red signal on the membrane represents the localization of CD19 CAR on the cell membrane. There is no red fluorescence signal on CD19 CAR negative T cells. Blue fluorescence represents nucleus.

(4) Analysis of Binding Kinetics with Fortebio Octet

Fortebio Octet was used to complete the kinetic analysis of R19mab binding to FMC63 scFv. In short, the biosensor was balanced offline in PBS buffer for 600 seconds, and then detected online for 60 seconds to establish a baseline. The purified FMC63 scFv recombinant protein was diluted to 50 μg/mL with PBS and then loaded onto the sensor for 60 seconds. Sensor loaded with FMC63 scFv was then exposed to different concentrations (from 15.6 nM to 0.975 nM, 5 concentrations) of R19mab for 600 seconds, and then the sensor was transferred to PBS to dissociate for 900 seconds for dissociation rate measurement. Data Analysis 6.2 evaluation software was used to analyze the data, and a 1:1 combination model was used for kinetic analysis.

Figure 9:
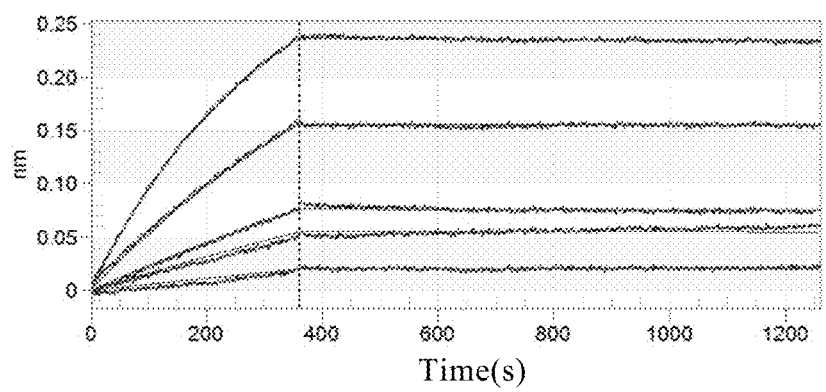
FIG. 9 shows the results of kinetic analysis of R19mab binding to FMC63 scFv.

Results:

As shown in FIG. 9, the equilibrium dissociation constant $K_D$ value of R19mab binding to FMC63 scFv reaches 43 pM, indicating that R19mab binds to FMC63 scFv with a high affinity. This result is consistent with the above-mentioned R19mab sensitivity detection results.

Example 4. Flow Cytometric Detection Kit for CD19 CAR Positive Cells Using R19mab (1) Preparing a kit (direct labeling method), which comprises the following reagents:
(a) a first container and a fluorescent labeled R19mab located in the first container (wherein the fluorescence can be different fluorescence such as FITC, PE, Alexa Fluor647, etc.);
(b) a second container and a NC (negative control reagent) located in the second container The kit is used as follows:
(I) $2×10^5$ cells to be tested were taken and washed twice with PBS (containing 1% blocking agent).
(II) The cells were resuspended with 100 μL PBS (containing 1 μL fluorescent labeled R19mab), and placed at 4° C. for 45 minutes.
(III) Washed twice with PBS.
(IV) Resuspended with 2004, PBS and detected by flow cytometry.

The kit is used to detect CD19 CAR-T cells, and the results show that the kit has the effects of high sensitivity and good specificity.

(2) Preparing a kit (secondary antibody method), which comprises the following agents:
(a) a first container and R19mab located in the first container;
(a) a second container and a fluorescent labeled secondary antibody located in the second container (wherein the fluorescence can be different fluorescence such as FITC, PE, Alexa Fluor647, etc.);
(c) a third container and a NC (negative control agent) located in the third container; and
(d) a fourth container and a blocking agent located in the fourth container.

The kit is used as follows:
(I) $2×10^5$ cells to be tested were taken and washed twice with PBS (containing 1% blocking agent).
(II) The cells were resuspended with 100 μL PBS (containing 1% blocking agent, 1 μL R19mab), and placed at 4° C. for 45 minutes.

(3) Washed twice with PBS.

(4) The cells were resuspended with 100 μL PBS (containing 0.1 μL fluorescent secondary antibody), and placed at 4° C. for 30 minutes in the dark.

(5) Washed with PBS twice.

(6) Resuspended with 200 μL PBS and detected by flow cytometry.

The kit was used to detect CD19 CAR-T cells, and the results show that the kit had the effects of high sensitivity and good specificity.

TABLE 1

| Antibody used in the experiment | | |
|---|---|---|
| Antibody | Cat. No. | Brand |
| R19mab | NA | BioSwan |
| FMC63 | MAB1794 | Merck & Millipore |
| Anti-rabbit IgG-peroxidase | A0545 | Sigma-Aldrich |
| Biotinylated Protein L. | M00097 | Genscript |
| Biotinylated CD19/Fc | CD9-H8259 | ACROBiosystems |

TABLE 1-continued

| Antibody used in the experiment | | |
|---|---|---|
| Antibody | Cat. No. | Brand |
| Streptavidin, PE | 12-4317-87 | eBioscience |
| Streptavidin, FITC | 405201 | BioLegend |
| Goat anti-rabbit IgG (H + L), Alexa Fluor 647 | A-21245 | Invitrogen |
| Goat anti-rabbit IgG (H + L), Alexa Fluor 488 | A-11034 | Invitrogen |
| Goat anti-rabbit IgG (H + L), Cy3 | 111-165-045 | Jackson ImmunoResearch |

All literatures mentioned in the present application are incorporated by reference herein, as though individually incorporated by reference. In addition, it should be understood that after reading the above teaching content of the present invention, various changes or modifications may be made by those skilled in the art, and these equivalents also fall within the scope as defined by the appended claims of the present application.

The invention claimed is:

1. An antibody having:
   (1) a heavy chain variable region comprising the following three complementarity determining regions or CDRs:
   CDR1 as shown in SEQ ID NO: 3;
   CDR2 as shown in SEQ ID NO: 4; and
   CDR3 as shown in SEQ ID NO: 5; and
   (2) a light chain variable region comprising the following three complementarity determining regions or CDRs:
   CDR1' as shown in SEQ ID NO: 6;
   CDR2' as shown in SEQ ID NO: 7; and
   CDR3' as shown in SEQ ID NO: 8;
   wherein the antibody is specific against a CD19-binding antibody, and the CD19-binding antibody is a murine monoclonal antibody FMC63 or FMC63 scFv.

2. A detection reagent for detecting CD19 CAR positive cells comprising a first detection reagent which is the antibody of claim 1.

3. A CD19 CAR detection kit comprising
   a first container containing the antibody of claim 1 and the antibody specifically binding to the extracellular antigen binding domain of CD19 CAR,
   and optional instructions.

4. The antibody of claim 1, wherein the light chain variable region has the amino acid sequence as shown in SEQ ID NO: 10.

5. The antibody of claim 1, wherein the heavy chain variable region has the amino acid sequence as shown in SEQ ID NO: 9.

6. A method for detecting CD19 CAR positive cells, comprising the steps of:
   (i) providing the detection reagent of claim 2; and
   (ii) detecting a cell population to be tested with the detection reagent, thereby obtaining a qualitative or quantitative detection result of CD19 CAR positive cells.

7. The antibody of claim 1, wherein the antibody comprises a single chain antibody (scFv), a Fab or (Fab')$_2$ fragment, a double-chain antibody, or a monoclonal antibody.

8. The antibody of claim 1, wherein the antibody is a rabbit-derived antibody.

9. The detection reagent of claim 2, wherein the detection reagent further comprises a second detection reagent specifically binding to the first detection reagent or a label coupled to the first detection reagent.

10. A recombinant protein having:
   (i) the antibody of claim 1; and
   (ii) a tag sequence assisting expression and/or purification.

11. An immunoconjugate comprising:
   (a) the antibody of claim 1; and
   (b) a coupling moiety selected from the group consisting of a detectable label, a drug, a toxin, a cytokine, a radionuclide, an enzyme, a magnetic bead, or agarose.

* * * * *

SEQUENCE LISTING

<160> NUMBER OF SEQ ID NOS: 10

<210> SEQ ID NO 1
<211> LENGTH: 242
<212> TYPE: PRT
<213> ORGANISM: Artificial Sequence
<220> FEATURE:
<223> OTHER INFORMATION: Amino acid sequence of CD19 scFv

<400> SEQUENCE: 1

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly

```
                210                 215                 220
Gly Ser Tyr Ala Met Asp Tyr Trp Gly Gln Gly Thr Ser Val Thr Val
225                 230                 235                 240

Ser Ser

<210> SEQ ID NO 2
<211> LENGTH: 248
<212> TYPE: PRT
<213> ORGANISM: Artificial Sequence
<220> FEATURE:
<223> OTHER INFORMATION: Nucleotide sequence of CD19 scFv

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser His His His His His His
            245

<210> SEQ ID NO 3
<211> LENGTH: 8
<212> TYPE: PRT
<213> ORGANISM: Artificial Sequence
<220> FEATURE:
<223> OTHER INFORMATION: Heavy chain CDR1

<400> SEQUENCE: 3

Gly Ile Asp Phe Arg Asn Tyr Gly
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Heavy chain CDR2

<400> SEQUENCE: 4

Phe Ser Ser Ser Gly Ser Thr
1               5

<210> SEQ ID NO 5
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 5

Ala Arg His Pro Gly Pro Thr Asn Gly Trp Lys Leu
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Light chain CDR1

<400> SEQUENCE: 6

Gln Ser Val Ser Gly Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: Light chain CDR2

<400> SEQUENCE: 7

Arg Ala Ser
1

<210> SEQ ID NO 8
<211> LENGTH: 14
<212> TYPE: PRT
<213> ORGANISM: Artificial Sequence
<220> FEATURE:
<223> OTHER INFORMATION: Light chain CDR3

<400> SEQUENCE: 8

Gln Ser Asn Tyr Asn Ser Gly Ser Ser Ser Ala Ala Ala
1               5                   10

<210> SEQ ID NO 9
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 9

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Phe Arg Asn Tyr Gly
            20                  25                  30
```

```
Val Ser Trp Val Arg Gln Ala Pro Gly Lys Gly Leu Glu Trp Ile Gly
        35                  40                  45

Ile Phe Ser Ser Gly Ser Thr Tyr Tyr Ala Thr Trp Ala Lys Gly
    50                  55                  60

Arg Phe Thr Ile Ser Lys Ala Ser Ser Thr Val Asp Leu Lys Met
65                  70                  75                  80

Thr Ser Leu Thr Thr Glu Asp Thr Ala Thr Tyr Phe Cys Ala Arg His
                85                  90                  95

Pro Gly Pro Thr Asn Gly Trp Lys Leu Trp Gly Pro Gly Thr Leu Val
            100                 105                 110

Thr Val Ser Ser
        115

<210> SEQ ID NO 10
<211> LENGTH: 112
<212> TYPE: PRT
<213> ORGANISM: Artificial Sequence
<220> FEATURE:
<223> OTHER INFORMATION: Light chain variable region

<400> SEQUENCE: 10

Asp Val Val Met Thr Gln Thr Pro Ala Ser Val Glu Ala Pro Val Gly
1               5                   10                  15

Gly Thr Val Thr Ile Lys Cys Gln Ala Ser Gln Ser Val Ser Gly Tyr
                20                  25                  30

Cys Ser Trp Tyr Gln Gln Lys Pro Gly Gln Pro Pro Lys Leu Leu Ile
        35                  40                  45

Tyr Arg Ala Ser Thr Leu Glu Ser Gly Val Pro Ser Arg Phe Ser Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ser Asn Tyr Asn Ser Gly Ser
                85                  90                  95

Ser Ser Ser Ala Ala Ala Phe Gly Gly Gly Thr Glu Val Val Val Lys
            100                 105                 110
```